(12) United States Patent
Pang et al.

(10) Patent No.: US 9,901,528 B2
(45) Date of Patent: Feb. 27, 2018

(54) COSMETIC COMPOSITION CONTAINING COMBINATION OF DISPERSION OF ACRYLIC POLYMER PARTICLES, THERMOPLASTIC ELASTOMER AND SEMI-CRYSTALLINE POLYMERS

(71) Applicant: L'ORÉAL, Paris (FR)

(72) Inventors: Christopher Pang, New York, NY (US); Hy Si Bui, Piscataway, NJ (US); Chunhua Li, Hillsborough, NJ (US)

(73) Assignee: L'ORÉAL, Paris (FR)

( * ) Notice: Subject to any disclaimer, the term of this patent is extended or adjusted under 35 U.S.C. 154(b) by 0 days.

(21) Appl. No.: 15/138,122

(22) Filed: Apr. 25, 2016

(65) Prior Publication Data
US 2017/0304181 A1    Oct. 26, 2017

(51) Int. Cl.
| | |
|---|---|
| A61K 8/72 | (2006.01) |
| A61K 8/81 | (2006.01) |
| A45D 7/00 | (2006.01) |
| A45D 40/30 | (2006.01) |
| A61K 8/19 | (2006.01) |
| A61K 8/41 | (2006.01) |
| A61K 8/31 | (2006.01) |
| A61K 8/49 | (2006.01) |
| A61Q 1/10 | (2006.01) |

(52) U.S. Cl.
CPC .............. *A61K 8/8152* (2013.01); *A61K 8/19* (2013.01); *A61K 8/31* (2013.01); *A61K 8/416* (2013.01); *A61K 8/4973* (2013.01); *A61K 8/8135* (2013.01); *A61K 8/8147* (2013.01); *A61K 8/8194* (2013.01); *A61Q 1/10* (2013.01); *A61K 2800/43* (2013.01); *A61K 2800/594* (2013.01)

(58) Field of Classification Search
None
See application file for complete search history.

(56) References Cited

U.S. PATENT DOCUMENTS

| | | | |
|---|---|---|---|
| 5,519,063 A | 5/1996 | Mondet et al. | |
| 6,274,131 B1 | 8/2001 | Piot et al. | |
| 6,482,400 B1 | 11/2002 | Collin | |
| 6,517,823 B1 | 2/2003 | Norman et al. | |
| 7,582,719 B1 | 9/2009 | Tan et al. | |
| 7,871,634 B2 | 1/2011 | Feng | |
| 7,871,635 B2 | 1/2011 | Stolz et al. | |
| 7,884,158 B2 | 2/2011 | Bui et al. | |
| 8,119,110 B2 * | 2/2012 | Blin | A61K 8/891 424/70.11 |
| 8,211,416 B2 | 7/2012 | Narebski et al. | |
| 8,313,735 B2 | 11/2012 | McDermott | |
| 8,526,499 B2 | 9/2013 | Jeon et al. | |
| 8,557,230 B2 | 10/2013 | Bui et al. | |
| 8,673,282 B2 | 3/2014 | Bui et al. | |
| 8,673,283 B2 | 3/2014 | Bui et al. | |
| 8,673,284 B2 | 3/2014 | Bui et al. | |
| 8,715,634 B2 | 5/2014 | Atis | |
| 8,758,739 B2 | 6/2014 | Bui et al. | |
| 8,778,323 B2 | 7/2014 | Bui et al. | |
| 8,932,573 B2 | 1/2015 | Alden-Danforth et al. | |
| 8,980,240 B2 | 3/2015 | Jager Lezer et al. | |
| 9,040,593 B2 | 5/2015 | Bui et al. | |
| 2005/0287093 A1 | 12/2005 | Lebre et al. | |
| 2006/0263438 A1 | 11/2006 | Biatry et al. | |
| 2006/0292095 A1 | 12/2006 | Biatry et al. | |
| 2007/0183997 A9 | 8/2007 | Lebre et al. | |
| 2007/0258923 A1 | 11/2007 | Bui et al. | |
| 2007/0258924 A1 | 11/2007 | Bui et al. | |
| 2007/0258925 A1 | 11/2007 | Bui et al. | |
| 2007/0258932 A1 | 11/2007 | Bui et al. | |
| 2007/0258933 A1 | 11/2007 | Bui et al. | |
| 2007/0258934 A1 | 11/2007 | Bui et al. | |
| 2008/0102048 A1 | 5/2008 | McDermott | |
| 2008/0102049 A1 | 5/2008 | McDermott | |
| 2008/0175808 A1 | 7/2008 | Pavel | |
| 2008/0219943 A1* | 9/2008 | De La Poterie | A61K 8/8152 424/70.7 |
| 2010/0028284 A1 | 2/2010 | Atis et al. | |
| 2010/0208817 A1 | 8/2010 | Jeon et al. | |
| 2010/0297041 A1 | 11/2010 | Smith et al. | |
| 2011/0243864 A1 | 10/2011 | Farcet et al. | |
| 2013/0188713 A1 | 7/2013 | Jeon et al. | |
| 2013/0236409 A1 | 9/2013 | Bui et al. | |
| 2015/0265519 A1 | 9/2015 | Bui et al. | |

FOREIGN PATENT DOCUMENTS

| | | |
|---|---|---|
| EP | 0 550 745 | 7/1993 |
| EP | 1 396 259 | 3/2004 |

OTHER PUBLICATIONS

International Search Report and Written Opinion dated Aug. 29, 2017 in PCT/US2017/027855.

* cited by examiner

*Primary Examiner* — Jeffrey T. Palenik
(74) *Attorney, Agent, or Firm* — Oblon, McClelland, Maier & Neustadt, L.L.P.

(57) ABSTRACT

The present invention relates to a cosmetic composition comprising a dispersion of acrylic polymer particles, a thermoplastic elastomer, a semi-crystalline polymer and an organic solvent. The compositions of the present invention may optionally contain at least one colorant. The invention also relates to a method for making up and/or enhancing the appearance of a keratinous substrate, in particular lashes, by applying these compositions to the keratinous substrate.

20 Claims, No Drawings

COSMETIC COMPOSITION CONTAINING COMBINATION OF DISPERSION OF ACRYLIC POLYMER PARTICLES, THERMOPLASTIC ELASTOMER AND SEMI-CRYSTALLINE POLYMERS

TECHNICAL FIELD

The present invention relates to a cosmetic composition and method for making up and/or enhancing the appearance of a keratinous substrate, comprising at least one dispersion of acrylic polymer particles, at least one thermoplastic elastomer, at least one semi-crystalline polymer and at least one organic solvent. The composition of the present invention may optionally contain at least one colorant.

BACKGROUND OF THE INVENTION

Makeup products, especially mascaras, are expected to have long wear, transfer resistance properties and most importantly provide good curling to eyelashes.

With regard to this expectation, currently marketed curling mascaras are typically emulsions comprised of water and a high amount of waxes (from 10-25%), specifically hard waxes. To enhance the desired properties, the mascaras often contain one or more film forming polymers and combinations of different waxes.

Illustrations of these polymers include silicone resins, polyacrylates, polyurethanes. See, U.S. Pat. No. 6,517,823, U.S. Pat. No. 6,274,131, U.S. Pat. No. 6,482,400 and US2010/0028284. However, the above-mentioned polymers and waxes, which are advantageous in providing the desired properties, make the finished products to be difficult to spread and provide an undesirable tacky feeling.

The inventors have found that the combination of a dispersion of acrylic polymer particles, a thermoplastic elastomer and a semi-crystalline polymer in an organic solvent and in the absence of water and hard waxes, provides a good curl (lift) which is stable over time.

The use of dispersion of acrylic polymer particles and silicone film forming polymers has previously been discussed, for example in PCT/EP2015/079341. In addition, the use of thermoplastic elastomers and semi-crystalline polymers has previously been disclosed, for example in U.S. Pat. No. 7,884,158, U.S. Pat. No. 8,211,416, US2008/0175808 and US2015/0265519.

Nevertheless, the inventors found that the association of the dispersion of acrylic polymer particles, di-block or/and tri-block thermoplastic elastomers having double glass transition temperatures (Tg) and the semi-crystalline polymer with melting temperature higher than 45° C., yields compositions having exceptional curling effect.

BRIEF SUMMARY OF THE INVENTION

The present invention relates to homogeneous cosmetic compositions for making up and/or enhancing the appearance of keratinous substrates comprising:
  (a) at least one dispersion of acrylic polymer particles;
  (b) at least one thermoplastic elastomer;
  (c) at least one semi-crystalline polymer; and
  (d) at least one organic solvent.

According to another aspect of the present invention, there is provided a method of making up and/or enhancing the appearance of a keratinous substrate, in particular eye lashes, comprising applying onto the keratinous substrate the above-disclosed composition, wherein the composition provides a great curl.

It is to be understood that both, the foregoing general description and the following detailed description are exemplary and explanatory only, and are not restrictive of the invention.

DESCRIPTION OF THE INVENTION

In the following description of the invention and the claims appended hereto, it is to be understood that the terms used have their ordinary and accustomed meanings in the art, unless otherwise specified.

"About" as used herein means within 10% of the indicated number (e.g. "about 10%" means 9%-11% and "about 2%" means 1.8%-2.2%).

As used herein, all ranges provided are meant to include every specific range within, and combination of subranges between, the given ranges. Thus, a range from 1-5, includes specifically 1, 2, 3, 4 and 5, as well as subranges such as and 2-5, 3-5, 2-3, 2-4, 1-4, etc.

"At least one" means one or more and thus includes individual components as well as mixture/combinations.

The term "glass transition temperature" (Tg) generally refers to the temperature at which amorphous material changes from a glassy solid state to a rubbery state. The temperature may be measured by standard techniques in the art, such a Differential Scanning Calorimetry (DSM), e.g., according to a standard protocol such as ASTM D3418-97 standard.

"Keratinous substrate" may be chosen from, for example, hair, eyelashes, lip, and eyebrows, especially eye lashes.

"Low Tg" or "Low Glass Transition Temperature" as used herein to describe the polymeric substances characterized by glass transition temperature (Tg) of lower than from about 6° C.

"High Tg" or "High Glass Transition Temperature" as used herein to describe the polymeric substances characterized by glass transition temperature (Tg) of from about 6° C. or higher "Polymers" as defined herein, include homopolymers and copolymers formed from at least two different types of monomers.

"The "Curling" or "curl" or "lift" of eyelashes as used herein, refers to a lifting and bending effect achieved after application of a mascara compositions or other cosmetics and care treatments.

"Anhydrous" or "water free" of "substantially water free", used interchangeably herein, mean that the composition contains no more than 5% of water.

"Wax free" or "essentially free of wax" or "devoid of wax" as it is used herein means that composition may contain no more than about 3% of wax.

The compositions and methods of the present invention can comprise, consist of, or consist essentially of the essential elements and limitations of the invention described herein, as well as any additional or optional ingredients, components, or limitations described herein or otherwise useful.

In an embodiment, the invention relates to a mascara composition comprising:
  (a) at least one dispersion of acrylic polymer particles;
  (b) at least one semi-crystalline polymer; and
  (c) at least one organic solvent;
wherein the ratio of at least one dispersion of acrylic polymer particles to the at least one semi-crystalline polymer is from about 4:10 to about 2.5:20, from about 5:13.6 to about 6.6:9.1, preferably is 9:2.76, most preferably is 3.3:13.6 and the ratio of at least one thermoplastic elastomer to the at least one semi-crystalline polymer is from about 5:1 to about 4:1, from about 2:1 to about 6:1 and from about 0.8:1 to about 0.4:1, by weight, relative to the total weight of the composition. All numerical values are weight percent solids (actives).

Another embodiment of this invention relates to a mascara composition comprising:
(d) from about 0.5% to about 80% of at least one dispersion of acrylic polymer particles;
(e) from about 0.5% to about 80% of at least one di-block thermoplastic elastomer;
(f) from about 0.1% to about 20% of at least one semi-crystalline polymer; and
(g) from about 4% to about 99% of at least one organic solvent.

In the particular embodiment, the invention relates to an anhydrous curling mascara composition comprising:
(h) from about 0.5% to about 80% of at least one dispersion of acrylic polymer particles;
(i) from about 0.5% to about 80% of at least one thermoplastic elastomer;
(j) from about 0.1% to about 20% of at least one semi-crystalline polymer; and
(k) from about 4% to about 99% of at least one organic solvent.

The invention also relates to an anhydrous curling mascara composition essentially free of wax.

Another aspect of the invention relates to a method of making the inventive composition.

Dispersion of Acrylic Polymer Particles

According to the present invention, cosmetic compositions containing at least one dispersion of acrylic polymer particles are provided. According to the present invention, the dispersions of acrylic polymer particles are dispersions of C1-C4 alkyl (meth)acrylate polymer particles stabilized with stabilizers based on isobornyl (meth)acrylate polymer in a hydrocarbon-based oil. The dispersion of acrylic polymer particles has been previously disclosed in PCT patent applications serial no. PCT/EP2014/077439 and PCT/EP2014/07800, the entire contents of which are hereby incorporated by reference.

According to preferred embodiments, the polymer of the particles is a C1-C4 alkyl (meth)acrylate polymer. The C1-C4 alkyl (meth)acrylate monomers may be chosen from methyl (meth)acrylate, ethyl (meth)acrylate, n-propyl (meth)acrylate, isopropyl (meth)acrylate, n-butyl (meth)acrylate and tert-butyl (meth)acrylate. Preferably, the monomer is a C1-C4 alkyl acrylate monomer. Preferably, the polymer of the particles is a methyl acrylate and/or ethyl acrylate polymer.

As per the instant invention, the polymer of dispersion of acrylic particles is rigid and it is characterized by glass transition temperature (Tg) higher than from about 6° C., more preferably higher than from about 15° C. and most preferably higher than from about 25° C.

The polymer of the particles may also comprise an ethylenically unsaturated acid monomer or the anhydride thereof, chosen preferably from ethylenically unsaturated acid monomers comprising at least one carboxylic, phosphoric or sulfonic acid function, such as, for example, crotonic acid, itaconic acid, fumaric acid, maleic acid, maleic anhydride, styrenesulfonic acid, vinylbenzoic acid, vinylphosphoric acid, acrylic acid, methacrylic acid, acrylamidopropanesulfonic acid or acrylamidoglycolic acid, and/or salts thereof. Preferably, the ethylenically unsaturated acid monomer is chosen from (meth)acrylic acid, maleic acid and maleic anhydride. The salts may preferably be chosen from salts of alkali metals, for example sodium or potassium; salts of alkaline-earth metals, for example calcium, magnesium or strontium: metal salts, for example zinc, aluminium, manganese or copper; ammonium salts of formula NH4+; quaternary ammonium salts; salts of organic amines, for instance salts of methylamine, dimethylamine, trimethylamine, triethylamine, ethylamine, 2-hydroxyethylamine, bis(2-hydroxyethyl)amine or tris(2-hydroxyethyl) amine; lysine or arginine salts.

The polymer of the particles may thus comprise or consist essentially of 80% to 100% by weight of C1-C4 alkyl (meth)acrylate and of 0 to 20% by weight of ethylenically unsaturated acid monomer, relative to the total weight of the polymer.

According to preferred embodiments, the polymer consists essentially of a polymer of one or more C1-C4 alkyl (meth)acrylate monomers.

According to preferred embodiments, the polymer consists essentially of a copolymer of C1-C4 (meth)acrylate and of (meth)acrylic acid or maleic anhydride.

The polymer of the particles may be chosen from, for example: methyl acrylate homopolymers; ethyl acrylate homopolymers; methyl acrylate/ethyl acrylate copolymers; methyl acrylate/ethyl acrylate/acrylic acid copolymers; methyl acrylate/ethyl acrylate/maleic anhydride copolymers; methyl acrylate/acrylic acid copolymers; ethyl acrylate/acrylic acid copolymers; methyl acrylate/maleic anhydride copolymers; and ethyl acrylate/maleic anhydride copolymers.

Preferably, the polymer of the particles is a non-crosslinked polymer.

The polymer of the particles of the dispersion preferably has a number-average molecular weight ranging from about 2000 to about 10,000,000, preferably ranging from about 150,000 to 500,000, including all ranges and subranges therebetween.

The polymer of the particles are preferably present in the dispersion in a content ranging from about 21% to about 58.5% by weight, preferably ranging from about 36% to about 42% by weight, relative to the total weight of the dispersion, including all ranges and subranges therebetween.

The stabilizer is preferably an isobornyl (meth)acrylate polymer chosen from isobornyl (meth)acrylate homopolymer and statistical copolymers of isobornyl (meth)acrylate and of C1-C4 alkyl (meth)acrylate present in an isobornyl (meth)acrylate/C1-C4 alkyl (meth)acrylate weight ratio of greater than 4. Preferably, the weight ratio ranges from about 4.5 to about 19, including all ranges and subranges therebetween.

Preferably, the stabilizer is chosen from, for example: isobornyl acrylate homopolymers; statistical copolymers of isobornyl acrylate/methyl acrylate; statistical copolymers of isobornyl acrylate/methyl acrylate/ethyl acrylate; statistical copolymers of isobornyl methacrylate/methyl acrylate, in the weight ratio described previously.

The stabilizing polymer preferably has a number-average molecular weight ranging from about 10,000 to about 400,000, preferably ranging from about 20,000 to about 200,000, including all ranges and subranges therebetween.

Although not wishing to be bound by any particular theory, it is believed that the stabilizer is in contact with the surface of the polymer particles and thus makes it possible to stabilize these particles at the surface in order to keep these particles in dispersion in the non-aqueous medium of the dispersion.

Preferably, the combination of the stabilizer and polymer of the particles present in the dispersion comprises from about 10% to about 50% by weight of polymerized isobornyl (meth)acrylate, and from about 50% to about 90% by weight of polymerized C1-C4 alkyl (meth)acrylate, relative to the total weight of the combination of the stabilizer and polymer of the particles.

Preferably, the combination of the stabilizer and polymer of the particles present in the dispersion comprises from about 15% to about 30% by weight of polymerized isobornyl (meth)acrylate, and from about 70% to about 85% by weight of polymerized C1-C4 alkyl (meth)acrylate, relative to the total weight of the combination of the stabilizer and polymer of the particles.

The oily medium of the polymer dispersion comprises a hydrocarbon-based oil.

The hydrocarbon-based oil is an oil that is liquid at room temperature (25° C.).

The term "hydrocarbon-based oil" means an oil formed essentially from, or even consisting of, carbon and hydrogen atoms, and optionally oxygen and nitrogen atoms, and not containing any silicon or fluorine atoms. It may contain, for example, alcohol, ester, ether, carboxylic acid, amine and/or amide groups.

The hydrocarbon-based oil may be chosen from, for example:

hydrocarbon-based oils containing from 8 to 14 carbon atoms, preferably:

branched C8-C14 alkanes, for instance C8-C14 isoalkanes of petroleum origin (also known as isoparaffins), for instance isododecane (also known as 2,2,4,4,6-pentamethylheptane), isodecane and, for example, the oils sold under the trade name Isopar or Permethyl, linear alkanes, for instance n-dodecane (C12) and n-tetradecane (C14) sold by Sasol under the respective references Parafol 12-97 and Parafol 14-97, and also mixtures thereof, the undecane-tridecane mixture, the mixtures of n-undecane (C1) and of n-tridecane (C13) obtained in Examples 1 and 2 of patent application WO 2008/155 059 from the company Cognis, the disclosure of which is hereby incorporated by reference, and mixtures thereof, short-chain esters (containing from 3 to 8 carbon atoms in total) such as ethyl acetate, methyl acetate, propyl acetate or n-butyl acetate, hydrocarbon-based oils of plant origin such as triglycerides consisting of fatty acid esters of glycerol, the fatty acids of which may have chain lengths varying from C4 to C24, these chains possibly being linear or branched, and saturated or unsaturated; these oils are especially heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion-flower oil and musk rose oil; shea butter, or else caprylic/capric acid triglycerides, for instance those sold by the company Stearineries Dubois or those sold under the names Miglyol 810®, 812® and 818® by the company Dynamit Nobel, synthetic ethers containing from 10 to 40 carbon atoms;

linear or branched hydrocarbons of mineral or synthetic origin, such as petroleum jelly, polydecenes, hydrogenated polyisobutene such as Parleam®, squalane and liquid paraffins, and mixtures thereof, synthetic esters such as oils of formula R1COOR2 in which R1 represents a linear or branched fatty acid residue containing from 1 to 40 carbon atoms and R2 represents an, in particular, branched hydrocarbon-based chain containing from 1 to 40 carbon atoms, on condition that R1+R2≥10, for instance purcellin oil (cetostearyl octanoate), isopropyl myristate, isopropyl palmitate, C12 to C15 alkyl benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, alkyl or polyalkyl heptanoates, octanoates, decanoates or ricinoleates such as propylene glycol dioctanoate; hydroxylated esters such as isostearyl lactate, diisostearyl malate and 2-octyldodecyl lactate; polyol esters and pentaerythritol esters, fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol.

Preferably, the hydrocarbon-based oil is apolar (formed solely from carbon and hydrogen atoms).

The hydrocarbon-based oil is preferably chosen from hydrocarbon-based oils containing from 8 to 14 carbon atoms, in particular the apolar oils described previously. Preferably, the hydrocarbon-based oil is isododecane.

The polymer particles of the dispersion preferably have an average size, especially a number-average size, ranging from about 50 to about 500 nm, preferably ranging from about 75 to about 400 nm, and preferably ranging from about 100 to about 250 nm, including all ranges and subranges therebetween.

In general, the dispersion according to the invention may be prepared in the following manner, which is given as an example.

The polymerization may be performed in dispersion, i.e. by precipitation of the polymer during formation, with protection of the formed particles with a stabilizer. In a first step, the stabilizing polymer is prepared by mixing the constituent monomer(s) of the stabilizing polymer, with a radical initiator, in a solvent known as the synthesis solvent, and by polymerizing these monomers. In a second step, the constituent monomer(s) of the polymer of the particles are added to the stabilizing polymer formed and polymerization of these added monomers is performed in the presence of the radical initiator.

When the non-aqueous medium is a non-volatile hydrocarbon-based oil, the polymerization may be performed in an apolar organic solvent (synthesis solvent), followed by adding the non-volatile hydrocarbon-based oil (which should be miscible with the said synthesis solvent) and selectively distilling off the synthesis solvent. A synthesis solvent which is such that the monomers of the stabilizing polymer and the free-radical initiator are soluble therein, and the polymer particles obtained are insoluble therein, so that they precipitate therein during their formation, is thus chosen. In particular, the synthesis solvent may be chosen from alkanes such as heptane or cyclohexane.

When the non-aqueous medium is a volatile hydrocarbon-based oil, the polymerization may be performed directly in the oil, which thus also acts as synthesis solvent. The monomers should also be soluble therein, as should the free-radical initiator, and the polymer of the particles obtained should be insoluble therein.

The monomers are preferably present in the synthesis solvent, before polymerization, in a proportion of about 5 to about 20% by weight. The total amount of monomers may be present in the solvent before the start of the reaction, or part of the monomers may be added gradually as the polymerization reaction proceeds. The free-radical initiator is preferably azobisisobutyronitrile or tert-butyl peroxy-2-ethylhexanoate.

The polymerization may be performed at a temperature ranging from about 70 to about 110° C.

The polymer particles are surface-stabilized, when they are formed during the polymerization, by means of the stabilizer.

The stabilization may be performed by any known means, and in particular by direct addition of the stabilizer, during the polymerization. The stabilizer is preferably also present in the mixture before polymerization of the monomers of the polymer of the particles. However, it is also possible to add it continuously, especially when the monomers of the polymer of the particles are also added continuously.

From about 10% to about 30% by weight, preferably from about 15% to about 25% by weight of stabilizer may be used, relative to the total weight of monomers used (stabilizer+polymer of the particles).

The polymer particle dispersion preferably comprises from about 30% to about 65% by weight, preferably from about 40% to about 60% by weight of solids, relative to the total weight of the dispersion.

Preferably, the oily dispersion may comprise a plasticizer, for example, a plasticizer chosen from tri-n-butyl citrate, tripropylene glycol monomethyl ether (INCI name: PPG-3 methyl ether) and trimethyl pentaphenyl trisiloxane (sold under the name Dow Corning PH-1555 HRI Cosmetic Fluid by the company Dow Corning). These plasticizers make it possible to improve the mechanical strength of the polymer film. The plasticizer, if present, may be present in the oily dispersion in an amount ranging from about 5% to about 50% by weight, relative to the total weight of the polymer of the particles.

According to preferred embodiments, the polymer of the particles is a C1-C4 alkyl (meth)acrylate polymer; the stabilizer is an isobornyl (meth)acrylate polymer chosen from isobornyl (meth)acrylate homopolymer and statistical copolymers of isobornyl (meth)acrylate and of C1-C4 alkyl (meth)acrylate present in an isobornyl (meth)acrylate/C1-C4 alkyl (meth)acrylate weight ratio of greater than 4. For these statistical stabilizing copolymers, the defined weight ratio makes it possible to obtain a polymer dispersion that is stable, especially after storage for seven days at room temperature (25° C.).

The dispersions according to the invention consist of particles, which are generally spherical, of at least one surface-stabilized polymer, in a non-aqueous medium.

Preferably, the amount of acrylic polymer particles present in the compositions of the present invention ranges from about 0.1% to about 35% by weight based on total weight of the composition, preferably about 1% to about 30% by weight based on the total weight of the composition, preferably about 5% to about 25% by weight based on the total weight of the composition, including all ranges and subranges therebetween.

Preferably, the dispersion of acrylic polymer particles is present in amounts of active material greater than 0.1%, preferably greater than 0.5%, and preferably greater than 1% based on the total weight of the composition, including all ranges and subranges in between.

Semi-Crystalline Polymers

The cosmetic composition of the invention includes at least one semi-crystalline polymer.

The term "semi-crystalline polymer" is used to mean polymers having a crystallizable portion, a crystallizable pendant chain, or a crystallizable sequence in its backbone, and an amorphous portion in the backbone, and that also presents a first-order reversible change-of-phase temperature, in particular for melting (solid-liquid transition). When the crystallizable portion is in the form of a crystallizable sequence of the polymer backbone, the amorphous portion of the polymer is in the form of an amorphous sequence. The semi-crystalline polymer is then a sequenced copolymer, e.g. of the diblock, triblock, or multiblock type, having at least one crystallizable sequence and at least one amorphous sequence. The term "sequence" generally means at least five identical repetition motifs. The crystallizable sequence(s) is/are then of a chemical nature that is different from the amorphous sequence(s).

The semi-crystalline polymer has a melting temperature greater than or equal to 30 degrees centigrade, in particular lying in the range 30 degrees centigrade to 100 degrees centigrade, preferably in the range 30 degrees centigrade to 80 degrees centigrade. The melting temperature is a first-order change-of-state temperature.

This melting temperature may be measured by any known method, and in particular by using differential scanning calorimetry (DSC).

Additionally, the semi-crystalline polymer applicable in this invention has molecular weight (MW) from about 30,000 (g/mol) to about 200,000 (g/mol).

The at least one semi-crystalline polymer may be employed in the cosmetic composition of the present invention in an amount ranging from about 0.1 to about 20 percent by weight, or from about 0.5 to about 10 percent by weight, or from about 1 to about 5 percent by weight, relative to the total weight of the composition, including all ranges and subranges therebetween.

By way of examples, such polymers are described in EP 1 396 259 and U.S. Pat. No. 8,980,240, the entire content of which is hereby incorporated by the references.

Semi-crystalline polymers containing crystallizable side chains may be homopolymers or copolymers comprising from 50 percent to 100 percent by weight of units resulting from the polymerization of one or more monomers bearing a crystallizable hydrophobic side chain.

Particularly suitable examples of semi-crystalline polymers useful in this invention are described in U.S. Pat. No. 8,932,573, the entire content of which is hereby incorporated by the references.

Polymers bearing in the skeleton at least one crystallizable block are especially block copolymers consisting of at least two blocks of different chemical nature, one of which is crystallizable. Examples are block copolymers of olefin or of cycloolefin containing a crystallizable chain, and copolymers containing at least one crystallizable block, the rest of the copolymer being amorphous (at room temperature). These copolymers may also contain two crystallizable blocks of different chemical nature.

In particular exemplary embodiments, the polymer comes from a crystallizable chain monomer selected from C14 to C30 saturated alkyl(meth)acrylates, including poly C10-30 alkyl(meth)acrylates.

Suitable examples of semi-crystalline alkyl(meth)acrylates include, but are not limited to, the Intelimer® or Doresco® products from the company Landec, such as those described in the brochure "Intelimer® Polymers" and/or are disclosed in U.S. patent application publication nos. 2006/0292095 and 2006/0263438, the disclosure of both of which is hereby incorporated by reference in their entirety. Specific examples include:

Doresco/Intelimer IPA 13-1®: polystearyl acrylate, with melting point of 49 degrees centigrade (° C.) and MW of 145,000; and Doresco/Intelimer IPA 13-6®: polybehenyl acrylate, having melting point of 66 degrees centigrade (° C.) and molecular weight (MW) of 45,000-126,000 g/mol.

In accordance with the present invention, it is also possible to use the semi-crystalline polymers obtained by copolymerization of stearyl acrylate and of acrylic acid or of NVP, or by copolymerization of behenyl acrylate and of acrylic acid or NVP, as described in document U.S. Pat. No. 5,519,063 or EP-A-0 550 745, the entire contents of both of which are hereby incorporated by reference.

The at least one semi-crystalline polymer, poly C10-30 alkyl acrylate may be employed in the cosmetic composition of the present invention in an amount ranging from about 0.1 to about 20 percent by weight, or from about 0.5 to about 10 percent by weight, or from about 1 to about 5 percent by weight, relative to the total weight of the composition, including all ranges and subranges therebetween.

Another example of semi-crystalline polymers useful in this invention are polymers and copolymers comprising at least one alkene monomer, in particular ethylene-based copolymers.

Such compounds can be chosen from copolymers of alkene and of vinyl acetate, in particular copolymers of ethylene and of vinyl acetate.

Use is made in particular of the copolymers of ethylene and of vinyl acetate preferably comprising more than 25 percent by weight of vinyl acetate, with respect to the total weight of the polymer.

Mention may be made, as example of ethylene/vinyl acetate copolymers, of those which are sold under the Dermacryl® LOR by the company Akzo Nobel and Elvax name by Du Pont de Nemours and in particular the compounds Elvax 40W, Elvax 140 W, Elvax 200 W, Elvax 205W, Elvax 210 W and Elvax 310.

Mention may also be made of the products sold under the Evatane name by Arkema, such as Evatane 28-800.

copolymers of ethylene and of octene, such as, for example, the products sold under the "Affinity" reference by Dow Plastics, such as, for example, Affinity GA 1900 and GA 1950.

The at least one semi-crystalline polymer, ethylene-based copolymer may be employed in the cosmetic composition of the present invention in an amount ranging from about 0.1 to about 20 percent by weight, or from about 0.5 to about 10 percent by weight, or from about 1 to about 5 percent by weight, relative to the total weight of the composition, including all ranges and subranges therebetween.

Applicable examples of semi-crystalline polymers useful in this invention are hyperbranched polymers, including hyperbranched functional polymer and these disclosed in US2015/0265519, the entire contents of which is hereby incorporated by the reference.

Generally, hyperbranched polymers are molecular constructions having a branched structure, generally around a core. Their structure generally lacks symmetry, the base units or monomers used to construct the hyperbranched polymer can be of diverse nature and their distribution is non-uniform. The branches of the polymer can be of different natures and lengths. The number of base units, or monomers, may be different depending on the different branching. While at the same time being asymmetrical, hyperbranched polymers can have any of the following: an extremely branched structure around a core; successive generations or layers of branching; layer of end chains.

According this invention, particularly useful are Hyperbranched Polyacids.

In a preferred embodiment, the compositions of the invention comprise at least one hyperbranched polyacid. Hyperbranched polyacid refers to the fact the functional groups of the hyperbranched functional polymer are substituted with carboxylic acid groups.

The at least one hyperbranched polyacid compound of the present invention has at least two carboxyl groups. Preferably, the hyperbranched polyacid has a carboxyl number of at least 3, more preferably of at least 10, more preferably of at least 50, and more preferably of at least about 150. According to preferred embodiments, the at least one hyperbranched polyacid has a carboxyl number between 50 and 250, preferably between 75 and 225, preferably between 100 and 200, preferably between 125 and 175, including all ranges and subranges there between such as 90 to 150.

Suitable examples of hyperbranched polyacids can be found in U.S. Pat. No. 7,582,719 and US2013/0236409, the entire contents of which are hereby incorporated by reference.

In an embodiment the hyperbranched polyacid is a semi-crystalline polymer having a glass transition temperature (Tg) of from about −30° C. to about 0'C, particularly from about −20° C. to about −1° C., more typically from about −15° C. to about −5° C., and a melting point of from about 45° C. to about 100° C., typically from about 50° C. to about 90° C., most typically from about 55° C. to about 85° C.

A particularly preferred acid functional olefinic polymer is C30+ olefin/undecylenic acid copolymer available from New Phase Technologies under trade name Performa V™-6112.

The at least one hyperbranched polymer, in including at least one hyperbranched polyacid polymer may be present in the composition of the invention in an amount ranging from about 0.5% to about 10% by weight, more particularly from about 1% to about 8% by weight, most particularly from about 2% to about 6% by weight, including all ranges and subranges therebetween, relative to the total weight of the composition.

According to another embodiment of this invention, suitable semi-crystalline polymers are polyamide resins, as these disclosed in U.S. Pat. No. 8,715,634 and U.S. Pat. No. 7,871,634, the entire contents of which are hereby incorporated by the references.

Specifically, the disclosed polymers are ester-terminated polyamides represented by the following formula (I):

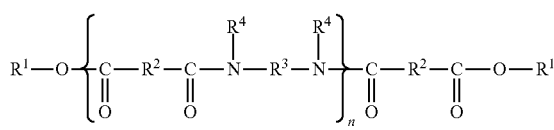

in which:

n is an integer which represents the number of amide units such that the number of ester groups present in the structuring polymer ranges from 10 percent to 50 percent of the total number of all the ester groups and all the amide groups comprised in the structuring polymer (e.g., n may be an integer ranging from 1 to 5, for example, an integer ranging from 3 to 5);

R1, which are identical or different, are each chosen from alkyl groups comprising at least 4 carbon atoms and alkenyl groups comprising at least 4 carbon atoms (e.g., each can be chosen from C12 to C22 alkyl groups, such as from C16 to C22 alkyl groups);

R2, which are identical or different, are each chosen from C4 to C42 hydrocarbon-based groups with the proviso that at least 50 percent of R2 are chosen from C30 to C42 hydrocarbon-based groups:

R3, which are identical or different, are each chosen from organic groups comprising atoms chosen from carbon atoms, hydrogen atoms, oxygen atoms and nitrogen atoms with the proviso that R3 comprises at least 2 carbon atoms; and R4, which are identical or different, are each chosen from hydrogen atoms, C1 to C10 alkyl groups and a direct bond to group chosen from R3 and another R4 such that when the at least one group is chosen from another R4, the nitrogen atom to which both R3 and R4 are bonded forms part of a heterocyclic structure defined in part by R4-N—R3, with the proviso that at least 50 percent of all R4 are chosen from hydrogen atoms.

Non-limiting examples of at least one polyamide polymer that may be used in the compositions of the present invention include the commercial products sold by Arizona Chemical under the names UNICLEAR 80 and UNICLEAR 100. These are sold, respectively, in the form of an 80 percent (in terms of active material) gel in a mineral oil and a 100 percent (in terms of active material) gel.

Another example of the ester-terminated polyamides is commercially available from Arizona Chemical under the name UNICLEAR VG (INCI Name: Ethylenediamine/ stearyl dimer dilinoleate copolymer) and OLEOCRAFT from Croda (INCI Name) Ethylenediamine/stearyl dimer dilinoleate copolymer).

Preferably, the at least one polyamide resin is present in an amount ranging from about 0.5 percent to about 20 percent by weight of active material with respect to the total weight of the composition, more preferably from about 2 percent to about 10 percent, more preferably from about 3 percent to about 6 percent, by weight of active material with respect to the total weight of the composition, including all ranges and subranges therebetween.

Thermoplastic Elastomers (Block Copolymer)

The thermoplastic elastomers of the present invention are block copolymers that are characterized by the presence of at least one "hard" segment, and at least one "soft" segment. Aside from their compositional nature, the hard and soft segments of the block copolymers of the present invention are defined in terms of their respective glass transition temperatures (Tg). More particularly, the hard segment has a Tg of 50 degrees centigrade or more, whereas the soft segment has a Tg of 0 degrees centigrade or less. The glass transition temperature Tg for the hard block can range from 50 degrees centigrade to 150 degrees centigrade; 60 degrees centigrade to 125 degrees centigrade: 70 degrees centigrade to 120 degrees centigrade; 80 degrees centigrade to 110 degrees centigrade The glass transition temperature Tg for the soft segment of the block copolymer can range from 0 degrees centigrade to −150 degrees centigrade; −10 degrees centigrade to −125 degrees centigrade; −25 to −100 degrees centigrade A more in depth explanation can be found in U.S. Pat. Nos. 5,294,438 and 6,403,070, the entire contents of which are hereby incorporated by reference.

The hard segments of the thermoplastic elastomer typically comprise vinyl monomers in varying amounts. Examples of suitable vinyl monomers include, but are not limited to styrene, methacrylate, acrylate, vinyl ester, vinyl ether, vinyl acetate, and the like.

Thermoplastic elastomers useful in the present invention are block copolymers e.g., di-block, tri-block, multi-block, radial and star block copolymers, and mixtures and blends thereof. A di-block thermoplastic elastomer is usually defined as an A-B type or a hard segment (A) followed by a soft segment (B) in sequence. A tri-block is usually defined as an A-B-A type copolymer or a ratio of one hard, one soft, and one hard segment. Multi-block or radial block or star block thermoplastic elastomers usually contain any combination of hard and soft segments, provided that the elastomers possess both hard and soft characteristics.

According to this invention, particularly useful are thermoplastic elastomers disclosed in U.S. Pat. No. 7,884,158 and U.S. Pat. No. 9,040,593, the entire contents of which are hereby incorporated by references.

In preferred embodiments, the at least one thermoplastic elastomer of the present invention may be chosen from the class of Kraton™ rubbers (Shell Chemical Company) or from similar thermoplastic elastomers. Kraton™ rubbers are thermoplastic elastomers in which the polymer chains comprise a di-block, tri-block, multi-block or radial or star block configuration or numerous mixtures thereof. The Kraton™ tri-block rubbers have polystyrene (hard) segments on each end of a rubber (soft) segment, while the Kraton™ di-block rubbers have a polystyrene (hard) segment attached to a rubber (soft) segment. The Kraton™ radial or star configuration may be a four-point or other multipoint star made of rubber with a polystyrene segment attached to each end of a rubber segment. The configuration of each of the Kraton™ rubbers forms separate polystyrene and rubber domains.

Each molecule of Kraton™ rubber is said to comprise block segments of styrene monomer units and rubber monomer and/or co-monomer units. The most common structure for the Kraton™ triblock copolymer is the linear A-B-A block type styrene-butadiene-styrene, styrene-isoprene-styrene, styrene-ethylenepropylene-styrene, or styrene-ethylenebutylene-styrene.

The Kraton™ di-block is preferably the AB block type such as styrene-ethylenepropylene, styrene-ethylenebutylene, styrene-butadiene, or styrene-isoprene. The Kraton™ rubber configuration is well known in the art and any block copolymer elastomer with a similar configuration is within the practice of the invention. Other block copolymers are sold under the tradename Septon (which represent elastomers known as SEEPS, sold by Kurary, Co., Ltd) and those sold by Exxon Dow under the tradename Vector™.

Other thermoplastic elastomers useful in the present invention include those block copolymer elastomers comprising a styrene-butylene/ethylene-styrene copolymer (triblock), an ethylene/propylene-styrene copolymer (radial or star block) or a mixture or blend of the two. (Some manufacturers refer to block copolymers as hydrogenated block copolymers, e.g. hydrogenated styrene-butylene/ethylene-styrene copolymer (tri-block)).

Particularly useful for this invention are hydrogenated styrene/butadiene copolymer (Kraton G1657) and hydrogenated styrene/isoprene copolymer (Kraton G1701), both commercially available from Kraton Polymers.

Preferably, the at least one thermoplastic elastomer resin is present in an amount ranging from about 0.5 percent to about 80 percent by weight of active material with respect to the total weight of the composition, more preferably from about 1 percent to about 60 percent, more preferably from about 2 percent to about 40 percent, and most preferably from about 3 percent to about 10 percent by weight of active material with respect to the total weight of the composition, including all ranges and subranges therebetween.

Organic Solvent

The composition of the invention also comprises a cosmetically acceptable solvent typically selected from a cosmetically acceptable organic solvent. Preferred organic solvents are non-aromatic oils such as, for example, non-aromatic hydrocarbon-based oils and non-aromatic silicone oils. In one embodiment, the non-aromatic oil is a volatile oil.

As used herein, the term "volatile oil" means an oil that is capable of evaporating on contact with keratin materials in less than one hour, at approximately room temperature and atmospheric pressure (760 mmHg). Volatile oils that may be used according to the disclosure include, but are not limited to, volatile cosmetic oils, which are liquid at room temperature and have a non-zero vapor pressure at room temperature and atmospheric pressure, said vapor pressure ranging, for example, from about 0.13 Pa to about 40,000 Pa (10-3 to 300 mmHg), such as from about 1.3 Pa to about 13,000 Pa (0.01 to 100 mmHg), or from about 1.3 Pa to about 1,300 Pa (0.01 to 10 mmHg). In contrast, non-volatile oils have a vapor pressure of less than about 1.33 Pa (0.01 mmHg).

According to various embodiments, the non-aromatic hydrocarbon-based oils may be chosen from:

- hydrocarbon-based oils comprising from 8 to 16 carbon atoms, for example, C8-C16 branched alkanes such as C8-C16 isoalkanes of petroleum origin (also known as isoparaffins), for instance isododecane (also known as 2,2,4,4,6-pentamethylheptane), isodecane, and isohexadecane, and, for example, the oils sold under the trade names Isopar® and Permethyl®; linear alkanes, for instance, n-dodecane (C12) and n-tetradecane (C14) sold by Sasol under the respective references Parafol 12-97 and Parafol 14-97, and mixtures thereof; the undecane-tridecane mixture, and mixtures of n-undecane (C11) and of n-tridecane (C13) obtained in Examples 1 and 2 of International Patent Application Publication No. WO 2008/155 059 assigned to the company Cognis, and mixtures thereof;
- linear and branched hydrocarbons of mineral or synthetic origin, such as petroleum jelly, polydecenes, hydrogenated polyisobutene such as Parleam®, squalane, liquid paraffins, and mixtures thereof;
- synthetic esters such as oils of formula R'1COOR'2 in which R'1 is chosen from linear and branched fatty acid residues comprising from 1 to 40 carbon atoms and R'2 is chosen from branched hydrocarbon-based chains comprising from 1 to 40 carbon atoms, with the proviso that R'1+R'2≥10, for instance purcellin oil (cetostearyl octanoate), isopropyl myristate, isopropyl palmitate, octyl palmitate, C12 to C15 alkyl benzoate, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, alkyl and polyalkyl heptanoates, octanoates, decanoates, and ricinoleates such as propylene glycol dioctanoate; hydroxylated esters such as isostearyl lactate, diisostearyl malate, and 2-octyldodecyl lactate; polyol esters and pentaerythritol esters;
- fatty alcohols that are liquid at room temperature, comprising a branched and/or unsaturated carbon-based chain comprising from 12 to 26 carbon atoms, for instance, octyldodecanol, isostearyl alcohol, oleyl alcohol, 2-hexyldecanol, 2-butyloctanol, and 2-undecylpentadecanol;
- higher fatty acids such as oleic acid, linoleic acid, linolenic acid, and mixtures thereof;
- hydrocarbon-based oils of plant origin such as triglycerides comprising fatty acid esters of glycerol, the fatty acids of which may have chain lengths comprising from 4 to 24 carbon atoms, these chains possibly being linear or branched, and saturated or unsaturated, for example, heptanoic and octanoic acid triglycerides, wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion flower oil, and musk rose oil; shea butter; and caprylic/capric acid triglycerides, for instance those sold by the company Stearineries Dubois or those sold under the names Miglyol 810®, 812® and 818® by the company Dynamit Nobel; and
- mineral oil.

According to one exemplary embodiment, the at least one non-aromatic oil is chosen from hydrocarbon-based oils comprising from 8 to 16 carbon atoms. For example, in at least one embodiment, the non-aromatic oil is selected from isodecane, isododecane, isohexadecane, and mixtures thereof.

The organic solvent may be present in the composition of the present invention in an amount ranging from about 4% to about 100% by weight, more preferably from about 10% to about 95% by weight, most preferably from about 15% to about 90% by weight, including all ranges and subranges therebetween, relative to the total weight of the composition.

Pigment(s)

The cosmetic compositions of the present invention may also contain at least one cosmetically acceptable colorant such as a pigment or dyestuff. Examples of suitable pigments include, but are not limited to, inorganic pigments, organic pigments, lakes, pearlescent pigments, iridescent or optically variable pigments, and mixtures thereof. A pigment should be understood to mean inorganic or organic, white or colored particles. Said pigments may optionally be surface-treated within the scope of the present invention, including but not limited to, surface treatments with compounds such as silicones, perfluorinated compounds, lecithin, and amino acids.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77,492 and 77,491; manganese violet (CI 77,742): ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on cochineal carmine (CI 75,570) and mixtures thereof.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

The precise amount and type of colorant employed in the compositions of the present invention will depend on the color, intensity and use of the cosmetic composition and, as a result, will be determined by those skilled in the art of cosmetic formulation. In an embodiment of the invention the pigment is present in an amount from about 5% to about 15% by weight, more particularly about 7% by weigh based on the total weight of the composition.

Additional Optional Additive

A composition according to the invention may also comprise at least one agent usually used in cosmetics, chosen, for example, from: reducing agents; thickeners; film-forming agents that are especially hydrophobic, or are softeners, antifoams, moisturizers, or UV-screening agents; ceramides; cosmetic active agents; peptizers; fragrances; proteins; vitamins; propellants; hydrophilic or lipophilic, film-forming or non-film-forming polymers; lipophilic or hydrophilic gelling agents; and preservatives. Non-limiting examples of preservatives include phenoxyethanol and caprylyl glycol. A non-exhaustive listing of such ingredients is found in U.S. Pat. No. 7,879,316, the entire content of which is hereby incorporated by reference. Additional examples of additives may be found in the International Cosmetic Ingredient Dictionary and Handbook (9th ed. 2002, and subsequent editions).

In an embodiment, the composition includes at least one preservative selected from Phenoxyethanol, caprylyl glycol, and a mixture thereof.

If present, the above additives are typically found in an amount for each of them of between about 0.01% and about 10% by weight, most typically from about 0.5% to about 5% by weight, including all ranges and subranges therebetween, by weight relative to the total weight of the composition. A person skilled in the art will take care to select the constituents of the composition such that the advantageous properties associated with the invention are not, or are not substantially, adversely affected.

EXAMPLES

The following Examples are intended to be non-restrictive and explanatory only, with the scope of the invention being defined by the claims.

As used in herein INCI US stands for International Nomenclature of Cosmetic Ingredients US.

TABLE 1

Mascara Composition

| INCI US | Control 1 | Control 2 | Inventive 1 | Inventive 2 | Inventive 3 | Inventive 4 | Inventive 5 | Inventive 6 | Inventive 7 | Inventive 8 |
|---|---|---|---|---|---|---|---|---|---|---|
| IRON OXIDES | 7 | 7 | 7 | 7 | 7 | 7 | 7 | 7 | 7 | 7 |
| DISTEARDIMONIUM HECTORITE | 0.17 | 0.17 | 0.17 | 0.17 | 0.17 | 0.17 | 0.17 | 0.17 | 0.17 | 0.17 |
| ISODODECANE | 11.60 | 11.60 | 11.60 | 11.60 | 11.60 | 11.60 | 11.60 | 11.60 | 11.60 | 11.60 |
| DISTEARDIMONIUM HECTORITE | 1.33 | 1.33 | 1.33 | 1.33 | 1.33 | 1.33 | 1.33 | 1.13 | 1.13 | 1.33 |
| PROPYLENE CARBONATE | 0.40 | 0.40 | 0.40 | 0.40 | 0.40 | 0.40 | 0.40 | 0.40 | 0.40 | 0.40 |
| POLY C10-30 ALKYL ACRYLATE (Interpolymer IPA 13-1 NG) | | | | | | | | | 5.00 | 10.00 |
| HYDROGENATED STYRENE/ISOPRENE COPOLYMER (KRATON G1701) | | 4.00 | 4.00 | 4.00 | 4.00 | 4.00 | 4.00 | 4.00 | 4.00 | 4.00 |
| POLY C10-30 ALKYL ACRYLATE (Interpolymer IPA 13-6) | | 5.00 | 10.00 | | | | | | | |
| ETHYLENE/VA COPOLYMER (and) PARAFFIN C28-52 | | | | | | | 5.00 | 10.00 | | |
| OLEFIN/UNDECYLENIC ACID COPOLYMER | | | | 5.00 | 10.00 | | | | | |

TABLE 1-continued

Mascara Composition

| INCI US | Control 1 | Control 2 | Inventive 1 | Inventive 2 | Inventive 3 | Inventive 4 | Inventive 5 | Inventive 6 | Inventive 7 | Inventive 8 |
|---|---|---|---|---|---|---|---|---|---|---|
| OIL DISPERSION (40% acrylic polymer solid particles/ 60% Isododecane) | 60 (24/36) | 60 (24/36) | 60 (24/36) | 60 (24/36) | 60 (24/36) | 60 (24/36) | 60 (24/36) | 60 (24/36) | 60 (24/36) | 60 (24/36) |
| ISODODECANE | 19.50 | 15.50 | 10.50 | 5.50 | 10.50 | 5.50 | 10.50 | 5.50 | 10.50 | 5.50 |

All numerical values in the above Table are weight percent active.

Method of Preparation of Mascaras

The dispersion of acrylic polymer particles has been prepared as previously disclosed in PCT patent applications serial no. PCT/EP2014/077439 and PCT/EP2014/07800, the entire contents of which are hereby incorporated by reference.

All ingredients were combined in a container, heated to 95° C. and placed in a speed mixer (DAC 150) and mixed at 2750 rpm for 5 mins until homogeneous. The mixture was then cooled to room temperature while mixing with a propeller blade. The tested compositions were filled into mascara containers assembled with curved elastomeric brushes.

Assessment of Curling Effect of Inventive Compositions Against Controls and Comparative Mascaras The results of curling properties of the mascara compositions are reported in Table 1.

The curling properties of the inventive compositions were tested against two controls (control 1 and control 2 as disclosed in Table 1) and against two anhydrous comparative mascaras, comparator A having volumizing effect and comparator B providing curling. Below is the structure of both comparators.

Comparator A: petroleum distillates, polyethylene, disteardimonium hectorite, carnauba wax, trihydroxystearin, propylene carbonate, pentaerythrityl hydrogenated rosinate, tall oil glycerides, tocopheryl acetate, phenoxyethanol, panthenol, propylparaben, pigments.

Comparator B: isododecane, trimethylsiloxysilicate, disteardimonium hectorite, dextrin palmitate/ethylhexanoate, microcrystalline wax, beeswax, polyethylene, propylene carbonate, *amellia japonica* seed oil, *chamomilla recutita* (*matricaria*) extract, nylon-6, aluminum distearate, pentaerythrityl hydrogenated rosinate, octyldodecyl isostearate, glyceryl isostearates, triethoxysilylethyl polydimethylsiloxyethyl hexyl dimethicone, caprylic/capric triglyceride, diethylaminoethyl methacrylate/hema/perfluorohexylethyl, methacrylate crosspolymer, pigments.

In order to compare the curling properties of the tested compositions, the evaluated mascara products were manually applies to fake eye lashes made of natural hair fibers (each fiber was 12 mm long). One sample of handmade eye lashes was stroked 30 times with the tested product, using elastomeric curved brush.

The lift (curve) of eyelashes was captured by a digital camera (Nicon D5500) and the angle of the lift was measured using a protractor and correlated to a scale describing the curling effect of the tested mascaras, as described in Table 2. The images were taken for untreated lashes, immediately after application of the tested mascaras and 10 minutes after the treatment. The tests were conducted through one day at ambient conditions (room temperature 20-25° C. and 20-30% relative humidity).

TABLE 2

Correlation between angle of curl and scale describing the curling effect

| Lift (curl) rating | Scale | Angle ° |
|---|---|---|
| none | 1 | 0-5 |
| slight | 2 | 6-10 |
| medium | 3 | 11-15 |
| good | 4 | 16-20 |
| great | 5 | 21-25 |
| excellent | 6 | 26-30 |
| Superb | 7 | >31 |

The curling properties of the tested mascara products are described in Table 3.

TABLE 3

The curling effect of tested mascara compositions

| Curling | Control 1 | Control 2 | Inventive 1 | Inventive 2 | Inventive 3 | Inventive 4 | Inventive 5 |
|---|---|---|---|---|---|---|---|
| Initial curl | 0-15° | 5-15° | 35-40° | 25-35° | 15-25° | 25-30° | 5-15° |
| Curl after 10 minutes | 0-15° | 5-15° | 35-40° | 25-35° | 10-20° | 10-20° | 5-15° |
| Initial curl | 3 | 3 | 7 | 7 | 5 | 6 | 3 |

TABLE 3-continued

The curling effect of tested mascara compositions

| | | | | | | | |
|---|---|---|---|---|---|---|---|
| Curl after 10 minutes | 3 | 3 | 7 | 7 | 4 | 4 | 3 |

| Curling | Inventive 6 | Inventive 7 | Inventive 8 | Comparator A | Comparator B |
|---|---|---|---|---|---|
| Initial curl | 25-30° | 15-20° | 30-40° | 0-5° | 20-25° |
| Curl after 10 minutes | 25-30° | 15-20° | 30-40° | 0-5° | 20-25° |
| Initial curl | 6 | 4 | 7 | 1 | 5 |
| Curl after 10 minutes | 6 | 4 | 7 | 1 | 5 |

As is shown in Table 3 the inventive compositions 1 and 2 containing Interpolymer IPA 13-6 at 5 and 10 percent respectively performed as good as the inventive composition 8 containing 10% of Interpolymer IPA 13-1 NG (the thermoplastic elastomer was used at 4 percent and the dispersion of acrylic polymer particles was present at 60 percent in all formulations). Their initial curling effect was greatly better than both controls' and comparators'. They were followed by Inventive compositions 6 and 4 (same performance), 3, 7 and 5 respectively.

While comparing the hold of the curling during the period of ten minutes, the inventive compositions 1, 2 and 8 demonstrated superiority against control and comparative formulations. They were followed by inventive compositions 6, then 3, 4 and 7 (all three had the same effect) and 5.

What is claimed is:

1. A cosmetic composition comprising:
    at least one dispersion of acrylic polymer particles comprising:
        (1) particles selected from the group consisting of:
    methyl acrylate homopolymers;
    ethyl acrylate homopolymers;
    methyl acrylate/ethyl acrylate copolymers;
    methyl acrylate/ethyl acrylate/acrylic acid copolymers;
    methyl acrylate/ethyl acrylate/maleic anhydride copolymers;
    methyl acrylate/acrylic acid copolymers;
    ethyl acrylate/acrylic acid copolymers;
    methyl acrylate/maleic anhydride copolymers;
    ethyl acrylate/maleic anhydride copolymers; and
    mixtures thereof; and
        (2) at least one stabilizer selected from the group consisting of:
    isobornyl acrylate homopolymers;
    statistical copolymers of isobornyl acrylate/methyl acrylate;
    statistical copolymers of isobornyl acrylate/ethyl acrylate;
    statistical copolymers of isobornyl acrylate/methyl acrylate/ethyl acrylate;
    statistical copolymers of isobornyl methacrylate/methyl acrylate; and
    mixtures thereof,
        at least one thermoplastic elastomer;
        at least one semi-crystalline polymer; and
        at least one organic solvent;
    wherein the ratio of at least one dispersion of acrylic polymer particles to the at least one semi-crystalline polymer is from about 4:10 to about 2.5:20 and the ratio of at least one thermoplastic elastomer to the at least one semi-crystalline polymer is from about 5:1 to about 4:1, by weight, relative to the total weight of the composition.

2. The composition of claim, 1 wherein the at least one dispersion of acrylic polymer particles is present in an amount from about 0.5% to about 80%, by weight, relative to the total weight of the composition.

3. The composition of claim, 1 wherein the at least one thermoplastic elastomer is present in an amount from about 0.5% to about 80%, by weight, relative to the total weight of the composition.

4. The composition of claim 3, wherein the at least one thermoplastic elastomer is selected from di-block copolymers and tri-block copolymer, and mixtures thereof.

5. The composition of claim 1, wherein the at least one semi-crystalline polymer is present in an amount from about 0.1% to about 20%, by weight, relative to the total weight of the composition.

6. The composition of claim 5, wherein the at least one semi-crystalline polymer is selected from C14 to C30 saturated alkyl (meth)acrylates, hyperbranched polymers, polyamide resins, ethylene-based copolymers, and mixtures thereof.

7. The composition of claim 1, wherein the at least one organic solvent is present in an amount from about 4% to about 99%, by weight, relative to the total weight of the composition.

8. The composition of claim 7, wherein the at least one organic solvent is selected from non-aromatic hydrocarbon oils and non-aromatic silicone oils.

9. The composition of claim 8, wherein at least one non-aromatic hydrocarbon oil is selected from isododecane, isodecane, isohexadacane, and mixtures thereof.

10. The composition of claim 1, wherein the composition is wax free mascara.

11. The nail composition of claim 1, wherein the polymer of the particles is a methyl acrylate and/or ethyl acrylate homopolymer.

12. The composition of claim 1, further comprising a pigment in an amount from about 5% to about 15%, by weight, relative to the total weight of the composition.

13. The composition of claim 1 comprising:
    from about 0.5% to about 80% of at least one dispersion of acrylic polymer particles;
    from about 0.5% to about 80% of at least one thermoplastic elastomer;
    from about 0.1% to about 20% of at least one semi-crystalline polymer;

from about 4% to about 99% of at least one organic solvent; and
from about 5% to about 15% of at least one pigment.

14. The composition of claim 1, wherein the at least one dispersion of acrylic polymer particles comprises:
   (1) particles selected from the group consisting of:
   methyl acrylate homopolymers;
   ethyl acrylate homopolymers; and
   mixtures thereof; and
   (2) at least one stabilizer selected from the group consisting of:
   isobornyl acrylate homopolymers;
   statistical copolymers of isobornyl acrylate/methyl acrylate;
   statistical copolymers of isobornyl acrylate/ethyl acrylate;
   statistical copolymers of isobornyl acrylate/methyl acrylate/ethyl acrylate;
   statistical copolymers of isobornyl methacrylate/methyl acrylate; and
   mixtures thereof.

15. The composition of claim 1, wherein the at least one dispersion of acrylic polymer particles comprises:
   (1) particles selected from the group consisting of:
   methyl acrylate/ethyl acrylate copolymers;
   methyl acrylate/ethyl acrylate/acrylic acid copolymers;
   methyl acrylate/acrylic acid copolymers;
   ethyl acrylate/acrylic acid copolymers; and
   mixtures thereof; and
   (2) at least one stabilizer selected from the group consisting of:
   isobornyl acrylate homopolymers;
   statistical copolymers of isobornyl acrylate/methyl acrylate;
   statistical copolymers of isobornyl acrylate/ethyl acrylate;
   statistical copolymers of isobornyl acrylate/methyl acrylate/ethyl acrylate;
   statistical copolymers of isobornyl methacrylate/methyl acrylate; and
   mixtures thereof.

16. The composition of claim 1, wherein the at least one dispersion of acrylic polymer particles comprises:
   (1) particles selected from the group consisting of:
   methyl acrylate/ethyl acrylate/maleic anhydride copolymers;
   methyl acrylate/maleic anhydride copolymers;
   ethyl acrylate/maleic anhydride copolymers; and
   mixtures thereof; and
   (2) at least one stabilizer selected from the group consisting of:
   isobornyl acrylate homopolymers;
   statistical copolymers of isobornyl acrylate/methyl acrylate;
   statistical copolymers of isobornyl acrylate/ethyl acrylate;
   statistical copolymers of isobornyl acrylate/methyl acrylate/ethyl acrylate;
   statistical copolymers of isobornyl methacrylate/methyl acrylate; and
   mixtures thereof.

17. The composition of claim 1, wherein the at least one dispersion of acrylic polymer particles comprises:
   (1) particles selected from the group consisting of:
   methyl acrylate homopolymers;
   ethyl acrylate homopolymers;
   methyl acrylate/ethyl acrylate copolymers;
   methyl acrylate/ethyl acrylate/acrylic acid copolymers;
   methyl acrylate/ethyl acrylate/maleic anhydride copolymers;
   methyl acrylate/acrylic acid copolymers;
   ethyl acrylate/acrylic acid copolymers;
   methyl acrylate/maleic anhydride copolymers;
   ethyl acrylate/maleic anhydride copolymers; and
   mixtures thereof; and
   (2) at least one stabilizer selected from the group consisting of:
   isobornyl acrylate homopolymers;
   statistical copolymers of isobornyl acrylate/methyl acrylate;
   statistical copolymers of isobornyl acrylate/methyl acrylate/ethyl acrylate;
   statistical copolymers of isobornyl methacrylate/methyl acrylate; and
   mixtures thereof.

18. The composition of claim 1, wherein the at least one dispersion of acrylic polymer particles comprises:
   (1) particles selected from the group consisting of:
   methyl acrylate homopolymers;
   ethyl acrylate homopolymers;
   methyl acrylate/ethyl acrylate copolymers;
   methyl acrylate/ethyl acrylate/acrylic acid copolymers;
   methyl acrylate/ethyl acrylate/maleic anhydride copolymers;
   methyl acrylate/acrylic acid copolymers;
   ethyl acrylate/acrylic acid copolymers;
   methyl acrylate/maleic anhydride copolymers;
   ethyl acrylate/maleic anhydride copolymers; and
   mixtures thereof; and
   (2) at least one stabilizer selected from the group consisting of:
   isobornyl acrylate homopolymers.

19. A method of making a mascara composition comprising combining:
   from about 0.5% to about 80% of at least one dispersion of acrylic polymer particles comprising:
   (1) particles selected from the group consisting of:
   methyl acrylate homopolymers;
   ethyl acrylate homopolymers;
   methyl acrylate/ethyl acrylate copolymers;
   methyl acrylate/ethyl acrylate/acrylic acid copolymers;
   methyl acrylate/ethyl acrylate/maleic anhydride copolymers;
   methyl acrylate/acrylic acid copolymers;
   ethyl acrylate/acrylic acid copolymers;
   methyl acrylate/maleic anhydride copolymers;
   ethyl acrylate/maleic anhydride copolymers; and
   mixtures thereof; and
   (2) at least one stabilizer selected from the group consisting of:
   isobornyl acrylate homopolymers;
   statistical copolymers of isobornyl acrylate/methyl acrylate;
   statistical copolymers of isobornyl acrylate/ethyl acrylate;
   statistical copolymers of isobornyl acrylate/methyl acrylate/ethyl acrylate;
   statistical copolymers of isobornyl methacrylate/methyl acrylate; and
   mixtures thereof,
   from about 0.5% to about 80% of at least one thermoplastic elastomer;
   from about 0.1% to about 20% of at least one semi-crystalline polymer;
   from about 4% to about 99% of at least one organic solvent; and
   from about 5% to about 15% of at least one pigment.

20. A method of curling eyelashes comprising applying the composition containing:
   from about 0.5% to about 80% of at least one dispersion of acrylic polymer particles comprising:

(1) particles selected from the group consisting of:
methyl acrylate homopolymers;
ethyl acrylate homopolymers;
methyl acrylate/ethyl acrylate copolymers;
methyl acrylate/ethyl acrylate/acrylic acid copolymers;
methyl acrylate/ethyl acrylate/maleic anhydride copolymers;
methyl acrylate/acrylic acid copolymers;
ethyl acrylate/acrylic acid copolymers;
methyl acrylate/maleic anhydride copolymers;
ethyl acrylate/maleic anhydride copolymers; and
mixtures thereof; and (2) at least one stabilizer selected from the group consisting of:
isobornyl acrylate homopolymers;
statistical copolymers of isobornyl acrylate/methyl acrylate;
statistical copolymers of isobornyl acrylate/ethyl acrylate;
statistical copolymers of isobornyl acrylate/methyl acrylate/ethyl acrylate;
statistical copolymers of isobornyl methacrylate/methyl acrylate; and
mixtures thereof, from about 0.5% to about 80% of at least one thermoplastic elastomer;
from about 0.1% to about 20% of at least one semi-crystalline polymer;
from about 4% to about 99% of at least one organic solvent; and
from about 5% to about 15% of at least one pigment.

* * * * *